United States Patent [19]

Hawk et al.

[11] 4,066,948
[45] Jan. 3, 1978

[54] CONCENTRATION MEASURING APPARATUS AND PROCESS

[75] Inventors: Roger M. Hawk, Mentor; Thomas A. Mitchell, Painesville, both of Ohio

[73] Assignee: Diamond Shamrock Corporation, Cleveland, Ohio

[21] Appl. No.: 633,954

[22] Filed: Nov. 20, 1975

[51] Int. Cl.$^2$ ............................................. G01N 27/42
[52] U.S. Cl. ..................................... 324/30 R; 324/29
[58] Field of Search ................ 324/30 R, 30 A, 30 B, 324/61 R; 328/27; 307/260, 261

[56] References Cited

U.S. PATENT DOCUMENTS

| | | | |
|---|---|---|---|
| 2,559,144 | 7/1951 | Baracket | 328/27 |
| 2,779,917 | 1/1957 | De Boisblanc | 324/30 A |
| 3,195,982 | 7/1965 | Nicholson | 324/30 R |
| 3,358,223 | 12/1967 | Birnstingl | 324/30 B |
| 3,499,733 | 3/1970 | Abbott et al. | 324/30 R |
| 3,515,988 | 6/1970 | Shawhan | 324/30 B |

*Primary Examiner*—M. Tokar
*Attorney, Agent, or Firm*—Roy Davis

[57] ABSTRACT

An apparatus and process for measuring the percent concentration of an electrolyte in solution is disclosed. The apparatus includes a crystal oscillator generating a square wave and a wave shaper to transform the wave into a monochromatic sine wave which passes through a two stage temperature compensated first buffer amplifier. The sine wave passes between electrodes which project into the solution under investigation and generates an output. A second buffer amplifier operates on the A.C. component of the output from the solution and is operatively connected to a half wave rectifier. The output of the half wave rectifier is proportional to the percent caustic. A temperature control device is utilized to hold the solution at a constant temperature.

An alternate embodiment utilizes two identical circuits with two different solutions. One circuit is used with a solution having a known concentration and one with an unknown concentration. The outputs are compared in a differential amplifier.

The process of this disclosure includes generating a square wave, converting the square wave to a monochromatic sine wave and amplifying the wave. The process further includes passing the monochromatic sine wave through a solution of an unknown concentration at a known temperature by means of electrodes projecting into the solution, removing any D.C. components, amplifying the output and converting it to a direct voltage repesenting the average of the A.C. wave. The magnitude of the output is then compared to a standard curve to note the concentration. Alternately, the monochromatic sine wave may be split and passed through a solution of unknown concentration to a solution of known concentration. The difference of the electrical outputs is taken and compared to calibration curves to determine the concentration.

21 Claims, 6 Drawing Figures

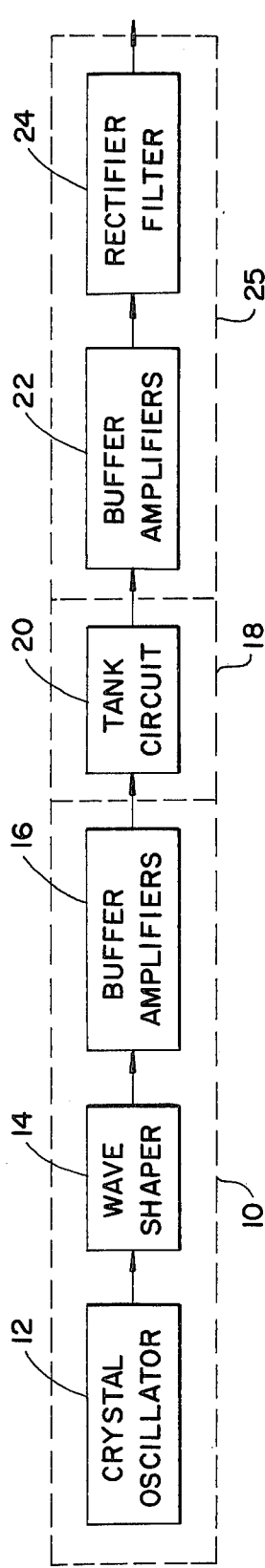
FIG. 1
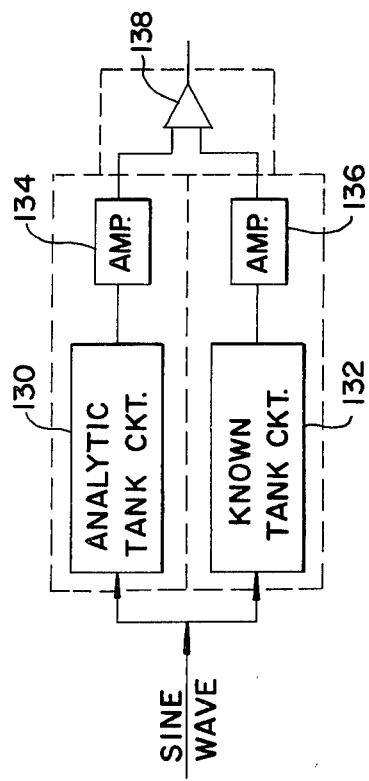
FIG. 4
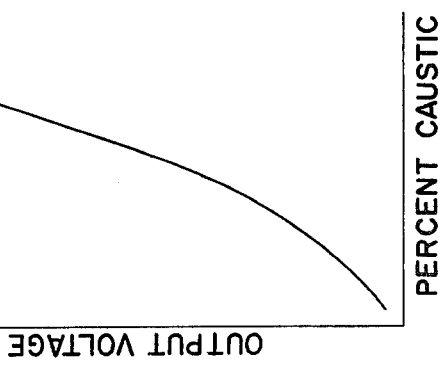
FIG. 5
FIG. 3

CONCENTRATION MEASURING APPARATUS AND PROCESS

BACKGROUND OF THE INVENTION

1. Field of the Invention

This invention is in the field of measuring the concentration of electrolyte solutions, such as sodium hydroxide. In particular, it relates to a device for measuring the change in power or voltage which is proportional to the concentration of the solution.

2. Description of the Prior Art

It is highly desirable to have a concentration measuring device which is efficient and accurate for large ranges of concentrations. Chemical analysis is a relatively long procedure and is not a practical solution to a large number of concentration measurements. It is particularly not applicable to a situation where fluid in a system is continuously monitored.

Previous systems such as U.S. Pat. No. 3,358,223 to Birnstingl proposed an electronic concentration meter to monitor the concentration of a solution. While there are advantages in the system disclosed, it has a serious disadvantage. Because the Birnstingl device directly measures conductivity, it has a limited range through which it can operate. Concentration levels over about 10 percent cause serious inaccuracies in the outputs of this type of concentration meter.

This invention provides an efficient and accurate system for determining the concentration of a solution. It is an electronic system which may be utilized to determine concentration quickly but does not have the disadvantage of being inaccurate over a certain level of concentration. This invention, instead of measuring the conductivity of the solution per se, measures the power absorption of the solution which is proportional to the concentration of the solution. Since voltage is directly related to power, both terms are used herein to refer to the absorption characteristic of the solutions.

By utilizing a constant temperature device, a linear relationship is obtained between the power absorbed by a solution and the percent of caustic in solution. Thus, accurate results can be obtained.

Alternately, a family of curves can be used to determine the concentrations if the temperature is not controlled.

SUMMARY OF THE INVENTION

This invention relates to a concentration measuring apparatus and method for solutions normally liquid which include a variable wave generator for generating a uniform alternating wave. Means for passing the wave through the solution causes some of the power in the wave to be absorbed by the solution. A means for measuring the remaining characteristics of the alternating wave after passing through the solution is utilized to determine the difference between the wave before it is passed through the solution and after.

The process of this invention includes generating a monochromatic alternating wave having known characteristics such as amplitude energy and power, passing the wave through the solution at a constant temperature, and measuring the characteristics of the alternating wave after it is passed through the solution. The difference in characteristics of the before and after waves is noted to determine the power absorbed by the solution which is proportional to the concentration of the solution.

BRIEF DESCRIPTION OF THE DRAWINGS

FIG. 1 is a block diagram of the apparatus of this invention;

FIG. 3 is a graph illustrating the relationship between percent caustic concentration in solution and output voltage;

FIG. 4 is an alternate embodiment of the block diagram of FIG. 2; and

FIG. 5 is a graph illustrating the type of approximation that was used in the prior art.

DETAILED DESCRIPTION OF THE DRAWINGS

Figure 2A:
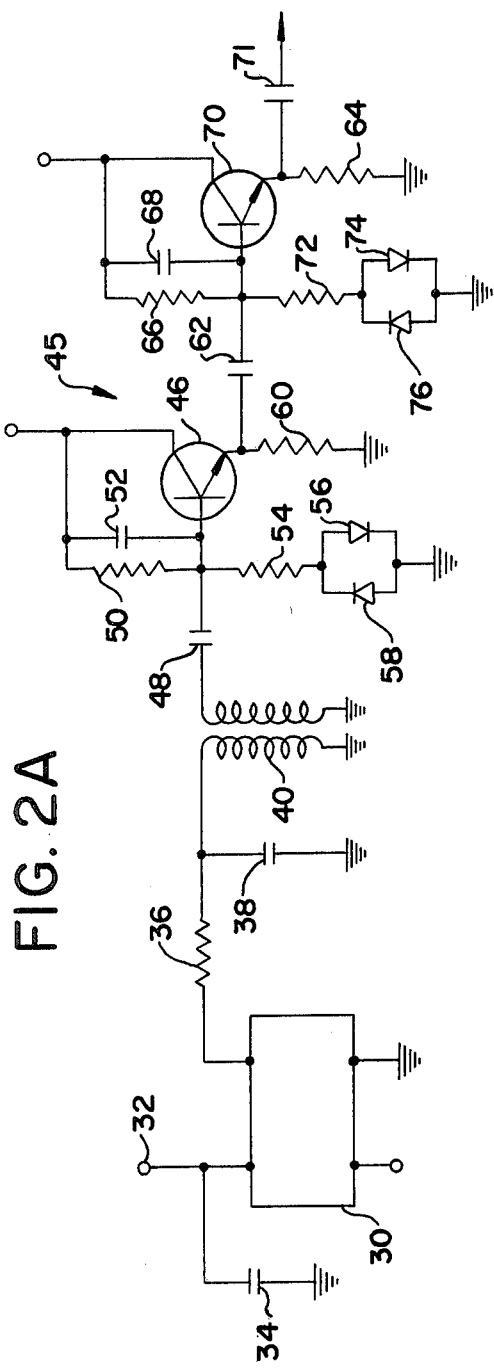
FIGS. 2A and 2B are a circuit diagram of one embodiment of this invention.

A block diagram of the invention is illustrated in FIG. 1. A means for creating 10 a monochromatic alternating wave of known characteristics generally includes a crystal oscillator 12, a wave shaper 14 and a buffer amplifier 16. The crystal oscillator 12 generates a square wave which is subsequently shaped by the wave shaper 14 and amplified by the buffer amplifier 16. Alternately, a monochromatic alternating wave which normally is a sine wave could be generated by other circuitry. The use of a crystal oscillator provides a wave which is amplitude and frequency stable and, therefore, does not need elaborate circuitry stabilization.

The output from the buffer amplifier 16 is operatively connected to a means for passing 18 the wave through a solution and includes a tank circuit 20 which has a constant temperature control device as will be described in more detail below. A buffer amplifier 22 and a combination rectifier-filter 24 combine to make a means for measuring 25 the output of the wave after it is passed through the solution. The measurement at the output is a D.C. component representing the average of the alternating wave and is proportional to the concentration of the solution.

Figure 2B:
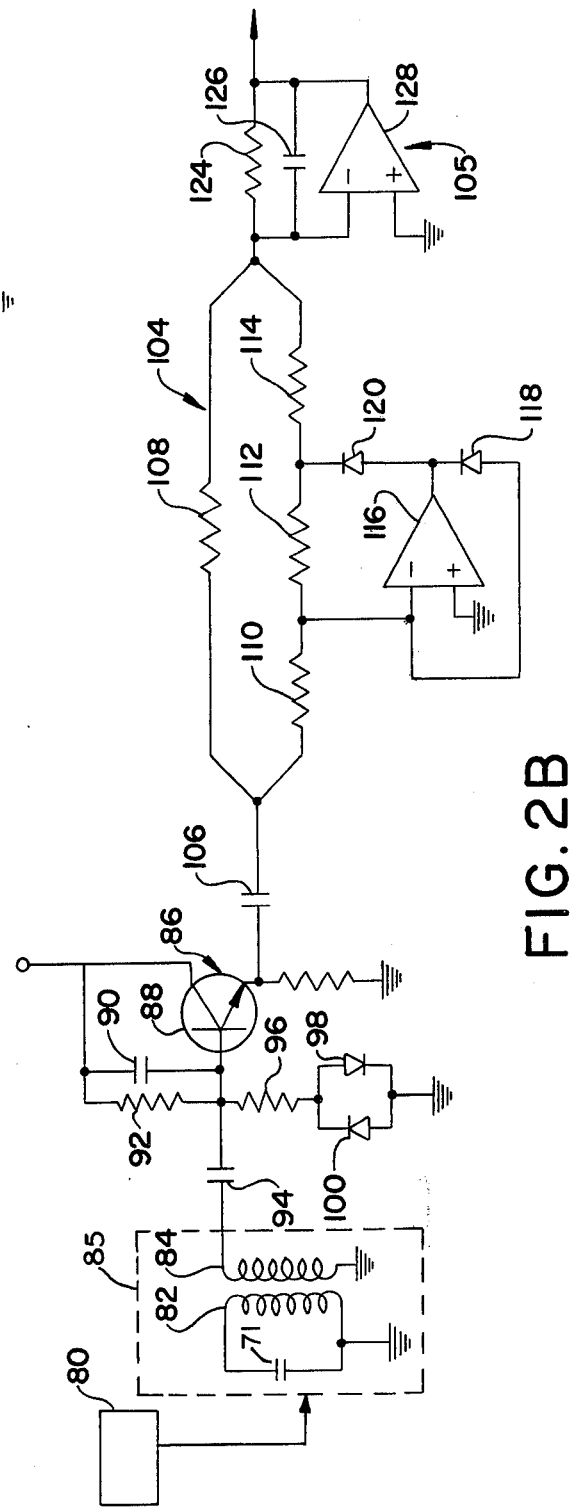

The circuitry of the block diagram of FIG. 1 is illustrated in FIGS. 2A and 2B and includes a crystal oscillator 30 which is a crystal controlled TTL device having an input 32 of positive 5 volts D.C. operatively attached to a 0.05 microfarad capacitor 34. The crystal oscillator generates an output through a 1 kilo-ohm resistor 36. The crystal oscillator is commercially available, for example, from the Motorola Corporation, Model No. K1100A. The wave generated is a 500 kilohertz square wave. Wave shaper 14 comprises a capacitor 38 and transformer 40 which is utilized to convert the square wave into a monochromatic sine wave. This type unit is commercially available from the ADC Corporation, Model No. BUG7-9.

Operatively attached to the wave shaper 14 is a two-stage buffer amplifier 45 which is utilized to maintain a constant amplitude of the sinusoidal wave. The first stage of the buffer amplifier includes an NPN transistor 46. It receives an input to its base through a capacitor 48 of about 0.01 microfared in order to remove any D.C. component. A resistor 50 of about 56 kilo-ohm and a parallel capacitor 52 of 100 picofarad leads to the collector. A 15 volt D.C. supply provides transistor bias. A 27 kilo-ohm resistor 54 is operatively connected to a pair of clamping diodes 56 and 58 which are temperature sensitive in the same manner as the transistor 46 so that any variations in temperature within the circuit will not change the bias at the base of the transistor 46. The transistor amplifiers are in an emitter follower configuration. A 3 kilo-ohm resistor 60 connects the emitter to ground.

A capacitor 62 is again utilized to filter out any D.C. components.

The second stage of the buffer amplifier is similar to the first in almost all respects and, likewise, includes a 15 volt D.C. which provides proper transistor bias. However, a 100 ohm resistor 64 is connected between the emitter and ground. In conjunction with this, a 56 kilo-ohm resistor 66 and parallel capacitor 68 of 100 picofarad lead to the collector of the transistor 70. A resistor 72 of about 27 kilo-ohm is utilized with a pair of clamping diodes 74 and 76 which maintain the constant voltage to the base of the transistor 70 regardless of circuit temperature. That is, the diodes are temperature sensitive in the same manner as the transistor. The output from the transistor 70 passes through a capacitor 71 of about 0.01 microfarad to electrodes which are placed in the solution under investigation. The electrodes extend through an insulated support and are normally made of platinum or some other material which is impervious to the effects of the solution per se. The electrodes are embedded in a solid ¾ inch acrylic rod which is axially located in a 4 inch circulation cylinder for adequate thermal equilibrium. Variations from these dimensions will be obvious to one skilled in the art. The exposed electrodes may be about ¼ inch long, 1/16 inch in diameter and have a separation of ¼ inch.

The solution being tested is maintained at a constant temperature by a control system 80. The temperature control system may be any one of numerous devices. For example, the temperature control device could use a heat exchanger with a temperature sensor in the solution which gives an electrical output in proportion to the solution temperature. Heat would thus be generated as necessary to maintain the desired temperature. A primary inductor 82 is used across the electrodes with the secondary inductor 84 in order to remove any D.C. component and obtain a pure A.C. signal. The dashed outline 85 indicates that portion of the circuit that is temperature controlled. A second buffer amplifier 86 is utilized and is identical to the first stage of the buffer amplifier described above. It includes an NPN transistor 88 having a collector connected through a 100 picofared capacitor 90 and a parallel 56 kilo-ohm resistor 92 to an output of a secondary coil 84. A 0.01 microfared capacitor 94 separates the coil 84 and transistor 88. A 27 kilo-ohm resistor 96 is utilized with a pair of clamping diodes 98 and 100 to hold the input to the base of the transistor 88 constant with a variable temperature.

A pair of analog devices 104 and 105 act as a half wave rectifier to convert the output from the transistor 88 to a pure D.C. signal. A 0.01 microfrarad capacitor 106 precedes the rectifier. The analog devices, as illustrated, are commercially available devices from Analog Devices, e.g. Model No. AD234J and AD920. The input of the first stage of the analog device is a 500 kilohertz wave and at the output becomes a 250 kilohertz pulsating D.C. wave. The first stage includes a 10 kilo-ohm resistor 108, 10 kilo-ohm resistor 110, 10 kilo-ohm resistor 112 and a 5 kilo-ohm resistor 114 operatively attached to an operational amplifier 116 and diodes 118 and 120.

The second device 105 of the half wave rectifier includes a 10 kilo-ohm resistor 124, a parallel .1 microfrarad capacitor 126 and an operational amplifier 128 operatively connected thereto. The output from the second analog device is the average value and is a representation of the concentration of the solution under investigation. As illustrated in FIG. 3, the relationship between the output voltage of the abovenoted circuitry and the percentage of caustic in solution is, for a large portion of its range, linear. This relatively simple relation makes the calculation or the equipment to do the calculations less elaborate than previously necessary. This substantially linear relation provides a distinct advantage over the prior art and greatly facilitates the measurement of concentration. FIG. 3 is a caustic monitor calibration curve at 30° C of sodium hydroxide. It represents an output voltage versus the percent caustic utilizing ⅛ inch long electrodes of about 1/16 inch diameter. The curve shows a slight curvature of percent caustic from about 22 to 28 percent which represents voltages of about 0.2 to 0.55 volts. From this percent caustic to greater percentages, there is a substantially linear relation between the percent caustic and the output voltage. This linear relation as noted above presents a very simple correlation between the caustic and the output voltage. While caustics are used for an example herein, this invention applies to other solutions, such a sodium chloride, sulfuric acid, hydrochloride acid and others. It is only necessary that the electrodes are properly spaced, made of a non-reacting material and have a length and diameter compatible with the solution tested.

A peak measurement of the amplitude of the output A.C. wave from the buffer amplifier 86 is also useable to determine the power absorption of the solution. However, peak measurement requires more elaborate equipment and is, therefore, more expensive.

The process of this invention is the generation of a monochromatic sine wave which is free of any D.C. component. The wave passes through the solution by means of probes in the solution. The solution, depending upon its concentration and its temperature, absorbs a certain amount of power or amplitude of the wave. The measurement of the output gives a direct indication, for that temperture, of the percent concentration of what is usually an electrolyte such as NaOH. It should also be noted that various components described above in the generation of the wave, the amplifiers and the rectification can be varied without deviating from the spirit of this invention. Moreover, the values given for the different components are for the purpose of illustration and are not necessarily required to practice this invention. Other values will be obvious to those skilled in the art. Moreover, this apparatus could be utilized with any solution that conducts current and is not limited to electrolytes.

FIG. 4 illustrates an alternate embodiment of a portion of the block diagram illustrated in FIG. 1. Instead of using a temperature control means with a single tank circuit, a monochromatic sine wave is split and passed through two separate tank circuits 130 and 132, one with a solution having an unknown concentration and one having a known concentration. After appropriate amplification by amplifiers 134 and 136, a differential amplifier 138 may be used therewith to determine the difference between the two power absorptions of the solutions. This difference gives the same type of measurement which is directly proportional to the percent concentration if the temperature has been controlled. If no temperature control is used with the differential embodiment, a family of curves, such as those shown in FIG. 5, will be necessary to identify the percent concentration. The primary benefit of the use of the dual tank circuits is the automatic compensation for amplitude and frequency variations which may occur at the input. The dual circuits would normally be used without the crystal oscillator which has a stable wave and does not usually need this type of compensation.

FIG. 5 illustrates a type of graphical representation that may be used with electronic concentration measuring devices of FIG. 4 for different concentrations at different temperatures. Each curve represents a different percent concentration. In order to use the curves, it is necessary to measure the output of a solution of unknown concentration for many different temperatures of the solution. The results are then plotted. The resulting curve is matched against a family of curves similar to that shown in FIG. 5 to see which one it most closely resembles.

The operations and process of this invention, in its most basic form, includes generating an alternating wave, passing the wave through a solution at a known controlled constant temperature, detecting the resultant wave after passing through the solution and measuring the difference in amplitudes or power between the input and output wave to the solution. More specifically, the process includes generating a square wave and shaping the wave to form a uniform sinusoidal wave. The wave is amplified, if necessary, and passed into a tank circuit which includes passing the wave through a solution of unknown concentration. The solution absorbs some of the power of the wave. The absorption of the wave is largely proportional to the concentration over a large range of concentrations. The process further includes either measuring the amplitude of the resultant wave after passing it through the solution of changing it to D.C. and measuring the resultant voltage. In order to obtain a practical concentration measurement, the process further includes comparing the resultant voltage measurement with a predetermined standard, usually a curve and noting the percent concentration.

It is important to note that the primary difference between the process of this invention and the prior art is that the conductivity is not in itself measured. As mentioned above, the conductivity has a tendency to become disproportionate to the concentration of the solution above certain percentages of concentration. The process of this invention does not have that limitation and is not dependent upon concentration.

The process of this invention further includes the alternate embodiment of passing the monochromatic sine wave through a first tank circuit having a solution of unknown concentration and a second tank circuit having a solution of known concentration. The output waves of the two solutions are then compared and the difference noted. The difference will be an indication of the concentration of the solution having an unknown concentration. However, because of temperature variations, different readings at different temperatures may be required and the resultant computation compared with a family of standard curves.

Other variations will be obvious to those skilled in the art. These variations are intended to be claimed within the spirit of this invention.

What is claimed is:

1. A concentration measuring apparatus comprising:
   a means for generating a monochromatic alternating wave having a known power;
   means for passing the wave through a liquid solution operatively connected to the means for generating;
   the means for generating including an electrode located in the solution for tranmission of the wave into the solution; the solution absorbing some of the power of the wave in an amount which is dependent on the concentration of the solution;
   means for measuring an indication of the power of the alternating wave after passing through the solution operatively connected to the means for passing in order to determine the difference between the power of the wave before it is passed through the solution and after and thus determine the amount of power of the wave absorbed by the solution at a known temperature.

2. The concentration measuring apparatus of claim 1 wherein the means for generating produces a monochromatic sine wave.

3. The concentration measuring apparatus of claim 2 wherein the means for generating further includes a crystal oscillator producing a square wave.

4. The concentration measuring apparatus of claim 3 wherein the means for generating further includes a wave shaper which changes the square wave to a sine wave and includes a primary and secondary coil.

5. The concentration measuring apparatus of claim 4 wherein the means for generating further includes a buffer amplifier operatively connected to the wave shaper.

6. The concentration measuring apparatus of claim 5 wherein the means for passing the wave through a solution includes a tank circuit including a pair of conductors, the means for passing the wave through the solution further including at least one buffer amplifier which aids in holding the wave amplitude at a constant value and the means for passing further including a means for maintaining the solution at a constant temperature.

7. The concentration measuring apparatus of claim 2 wherein the means for passing further includes a buffer amplifier and includes at least one transistor amplifier having a diode clamp operatively connected thereto in order to compensate for temperature variations within the circuitry and thus avoid inaccuracies from this cause.

8. The concentration measuring apparatus of claim 7 wherein the means for passing further includes a buffer amplifier and includes two series transistor amplifiers.

9. The concentration measuring apparatus of claim 8 wherein the means for measuring includes a half wave rectifier for converting the alternating voltage to a direct current component.

10. The concentration measuring apparatus of claim 9 wherein the half wave rectifier includes a first analog device and a second analog device in series therewith which converts the alternating monochromatic wave to its average which is proportional to the concentration of the solution.

11. The concentration measuring apparatus of claim 2 wherein the means for passing the wave through a solution further includes a temperature compensation means for holding the solution at a predetermined temperature.

12. The concentration measuring apparatus of claim 2 wherein the means for passing the wave through a solution includes a first tank circuit and a second tank circuit, the first tank circuit operating in conjunction with the unknown solution and the second tank circuit acting in conjunction with a solution of known concentration.

13. The concentration measuring apparatus of claim 12 wherein the means for measuring the output includes a differential amplifier which receives the output from the first tank circuit and the second circuit and produces an output representing the differences between the two tank circuits.

14. The process of measuring the percent concentration of a liquid solution including:
generating a monochromatic alternating wave having a constant known amplitude;
passing the wave into the solution by an electrode located in the solution, the solution absorbing some of the energy of the wave;
measuring a characteristic of the energy of the wave after passing through the solution and comparing energies of the wave before passing through the solution and after to give an indication of the absorption of the solution and therefore its concentration at a known temperature and comparing the absorption with a known correlation between the wave amplitude and the concentration of the solution.

15. The process of claim 14 wherein the generating of the monochromatic alternative wave includes generating a square wave and altering the wave to produce a sine wave.

16. The process of claim 15 wherein the altering of the wave includes passing the wave through a buffer amplifier.

17. The process of claim 16 wherein passing the wave through a solution includes holding the solution at a constant known temperature.

18. The process of claim 17 wherein the measurement of the output includes converting the alternating wave to a D.C. component.

19. The process of claim 18 wherein comparing the amplitude includes comparing the output of the half wave rectifier with the calibration curve to determine the concentration.

20. The process of measuring the percent concentration of a liquid solution including generating a monochromatic alternating wave having a known constant amplitude;
passing the wave through a first solution of unknown concentration by means of an electrode located in the first solution;
passing the wave through a solution of known concentration by means of an electrode located in the second solution at the same temperature as the unknown concentration;
comparing the outputs of the waves after passing through each of the solutions and noting the difference;
comparing the difference with a calibration curve to determine the concentration of the second solution.

21. The process of claim 20 wherein the wave is sinusoidal and the differences between the outputs of the first and second solutions are both measured at different temperatures and the resultant data is compared with calibration curves to determine the concentration of the second solution.

* * * * *

UNITED STATES PATENT AND TRADEMARK OFFICE
CERTIFICATE OF CORRECTION

PATENT NO. : 4,066,948
DATED : Jan. 3, 1978
INVENTOR(S) : Roger M. Hawk and Thomas A. Mitchell It is certified that error appears in the above-identified patent and that said Letters Patent are hereby corrected as shown below:

Column 8, line 23, delete "second" and insert therefor "first".

Column 8, line 29, delete "second" and insert therefor "first".

Signed and Sealed this

Twenty-seventh Day of June 1978

[SEAL]

Attest:

RUTH C. MASON
Attesting Officer

DONALD W. BANNER
Commissioner of Patents and Trademarks